(12) United States Patent
Zhu (10) Patent No.: US 11,944,569 B2
(45) Date of Patent: Apr. 2, 2024

(54) HAND WARMER CAPABLE OF DISMOUNTING BATTERY

(71) Applicant: Guangdong Aoyun Technology Co., Ltd., Huizhou (CN)

(72) Inventor: Xueping Zhu, Chenzhou (CN)

(73) Assignee: Guangdong Aoyun Technology Co., Ltd., Huizhou (CN)

( * ) Notice: Subject to any disclaimer, the term of this patent is extended or adjusted under 35 U.S.C. 154(b) by 83 days.

(21) Appl. No.: 17/805,685

(22) Filed: Jun. 6, 2022

(65) Prior Publication Data

US 2023/0404796 A1 Dec. 21, 2023

(30) Foreign Application Priority Data

May 30, 2022 (CN) .......................... 202221311804.X (51) Int. Cl.
*A61F 7/00* (2006.01)
(52) U.S. Cl.
CPC ...... *A61F 7/007* (2013.01); *A61F 2007/0036* (2013.01); *A61F 2007/0078* (2013.01)
(58) Field of Classification Search
CPC ...... A61F 2007/0036; A61F 2007/0078; A61F 7/007; A61F 2007/0075
See application file for complete search history.

(56) References Cited

U.S. PATENT DOCUMENTS

| 2008/0024962 A1* | 1/2008 | Wang | H05K 5/061 |
| | | | 361/600 |
| 2010/0024795 A1* | 2/2010 | Lee | A61F 7/03 |
| | | | 126/208 |

FOREIGN PATENT DOCUMENTS

| CN | 215131370 U | * 12/2021 |
| CN | 216455575 U | * 5/2022 |

* cited by examiner

*Primary Examiner* — Joseph A Stoklosa
*Assistant Examiner* — Adam J Avigan
(74) *Attorney, Agent, or Firm* — Zhigang Ma (57) ABSTRACT

The utility model discloses a hand warmer with detachable battery, which relates to the hand warmer field, and comprises a shell, wherein the outer side of the shell is provided with a hardware piece, the inner side of the shell is fixedly provided with a PCB motherboard, and the inner side of the shell is also provided with a detachable battery compartment; the bottom of the shell is provided with an opening structure, and a battery cover is clamped at the opening, and the battery cover can be detached from the opening; the outer side of the shell is also provided with silica gel, which is formed by splicing two plastic shells, and the silica gel is arranged outside the connecting seam of the shell. By arranging the battery cover, which can be directly detached from the shell, the utility model is convenient to replace the battery, and can be used for hand warmers all day. Moreover, the battery cover can be installed in two directions during installation by arranging the structure such as the limiting clamping groove and the positioning wave bead, and the battery cover can be easily disassembled by adopting the limiting mode in two directions, so that the installation is more stable.

6 Claims, 11 Drawing Sheets

HAND WARMER CAPABLE OF DISMOUNTING BATTERY

This application claims the benefit and priority of Chinese Patent Application Number 202221311804.X, filed on May 30, 2022 with China National Intellectual Property Administration, the disclosures of which are incorporated herein by reference in their entireties.

FIELD OF THE UTILITY MODEL

The utility model relates to the field of hand warmers, in particular to hand warmers with detachable batteries.

BACKGROUND OF THE RELATED ART

Hand warmer is an automatic heating and health care product developed by using physical and chemical principles. With the development of lithium battery technology, hand warmers also use lithium batteries for heating, and the heating time is relatively long. However, the existing hand warmers lithium battery is fixedly installed in the shell, and the lithium battery cannot be disassembled. In the case of cold weather in winter, the hand warmers can be used for a long time, while the hand warmers can only be charged directly after they are out of power, so they can't meet the long-term use requirements and all-weather use. Therefore, a hand warmer which can replace the battery is needed.

SUMMARY OF THE UTILITY MODEL

The utility model aims to provide a hand warmer with detachable battery, so as to solve the problems in the above background technology.

In order to achieve the above purpose, the utility model provides the following technical scheme: the hand warmer with detachable battery comprises a shell, the outer side of which is provided with a hardware piece, the inner side of which is fixedly provided with a PCB motherboard, and the inner side of which is also provided with a detachable battery compartment, the bottom of which is provided with an opening structure, and the opening is clamped with a battery cover which can be detached from the opening, and the outer side of which is also provided with silica gel.

Preferably, the shell is formed by splicing two plastic shells, and the silica gel is arranged outside the connecting seam of the shell.

Preferably, the upper end of the shell is also provided with an upper cover, and silica gel is fixedly installed on the outer sides of the upper cover and the battery cover.

Preferably, positioning points are fixedly installed at the upper end of the inner side of the housing, positioning grooves matched with the positioning points are formed at the top and both sides of the battery compartment, and charging interfaces matched with each other are also arranged inside the housing and on the battery compartment for supplying power to the PCB motherboard and hardware chips.

Preferably, one side of the bottom of the shell is fixedly provided with an outward protruding tail buckle with an arc structure, and the outer side of the shell is also provided with a guide groove; the inner edge of the battery cover is provided with a bump matched with the guide rail groove, and one side of the battery cover is provided with a clamping groove matched with the tail buckle.

Preferably, the inner side wall of the bottom of the shell is provided with a clamping groove, and the top of the battery cover is fixedly provided with a clamping block matched with the clamping groove, and the clamping block is provided with positioning beads. When installing, the clamping block is inserted into the clamping groove, and the battery cover is pushed laterally, and the positioning beads are clamped together.

Preferably, the inner side wall of the bottom of the shell is provided with a clamping groove, and the top of the battery cover is fixedly provided with a clamping block matched with the clamping groove, and the clamping block is provided with positioning beads. When installing, the clamping block is inserted into the clamping groove, and the battery cover is rotated, and the positioning beads are clamped together.

Compared with the prior art, the utility model has the advantages that:

By arranging the battery cover, which can be directly detached from the shell, the utility model is convenient to replace the battery, and can be used for hand warmers all day. Moreover, the battery cover can be installed in two directions by setting the structure of limiting slot, positioning wave bead, etc., and the battery cover can be easily disassembled by adopting the limiting mode in two directions, so that the installation is more stable. However, when being impacted, the impact force is unidirectional, so it is not easy to open during impact, and the battery can be prevented from falling.

In the picture: 1. Shell; 2. Wupian; 3. Battery compartment; 4. Battery cover; 5. PCB motherboard; 6. Silica gel; 7. Tail buckle; 7A. Block; 71. Positioning wave beads; 8. Guide groove; 9. Charging interface; 10. Positioning point; 11. Positioning groove; 12. Upper cover.

DETAILED DESCRIPTION OF THE PREFERRED EMBODIMENTS

The following will clearly and completely describe the technical scheme in the embodiment of the utility model with reference to the drawings in the embodiment of the utility model. Obviously, the described embodiment is only a part of the embodiment of the utility model, but not the whole embodiment. Based on the embodiments in this utility model, all other embodiments obtained by ordinary technicians in this field without creative labor belong to the scope of protection of this utility model.

Figure 1:
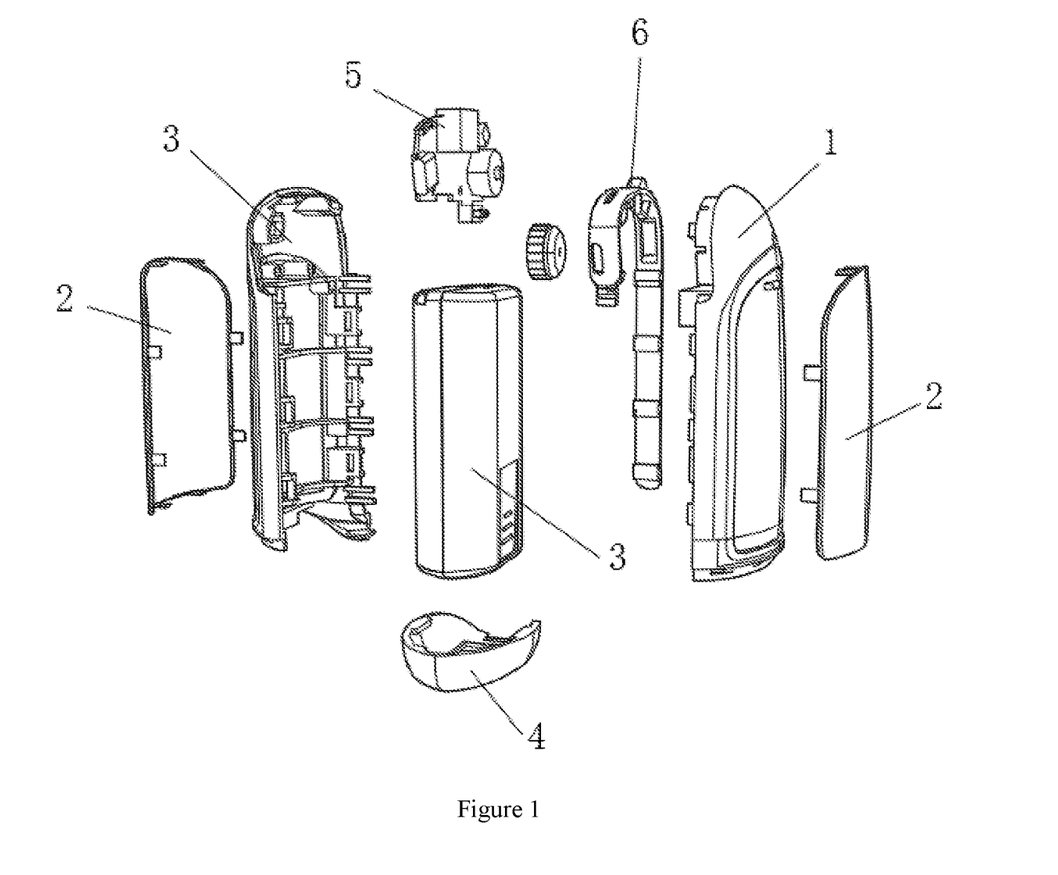
FIG. 1 is an explosion diagram of the shell of the utility model.
Figure 5:
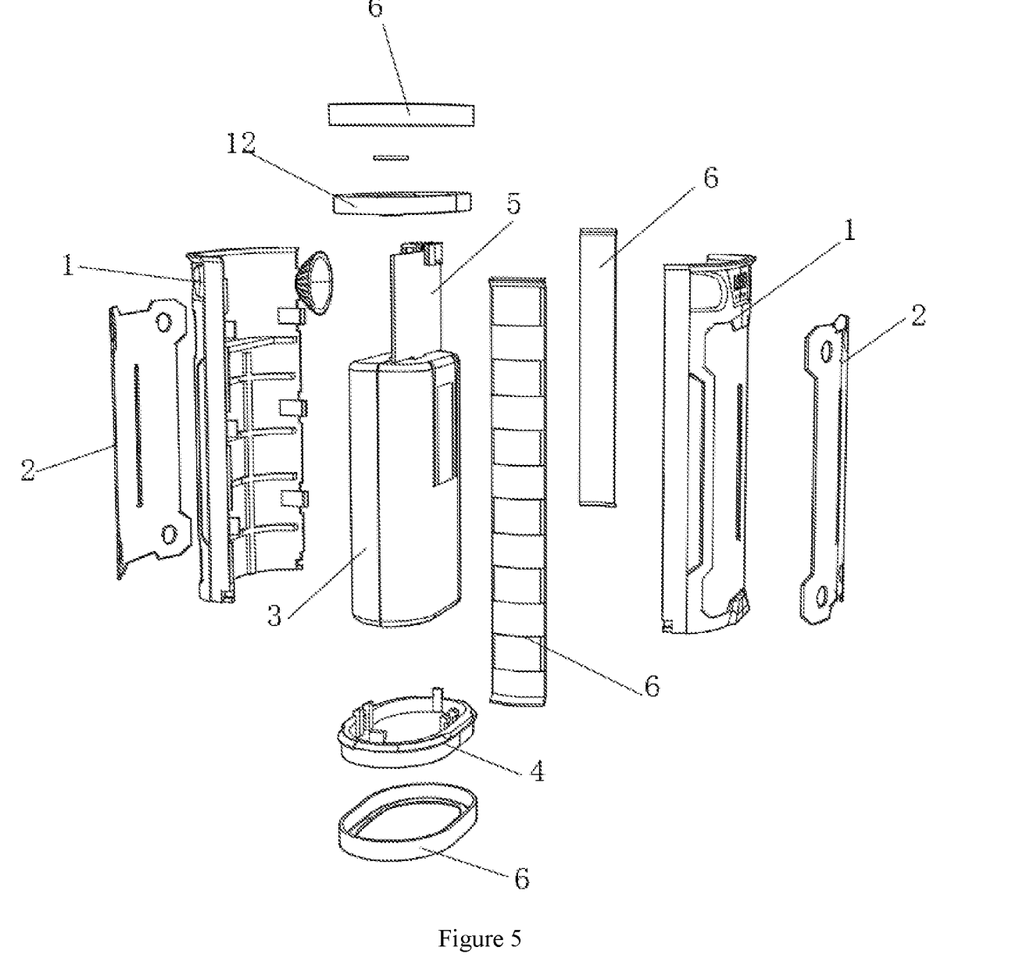
FIG. 5 is another explosion diagram of the shell of the utility model.
Figure 9:
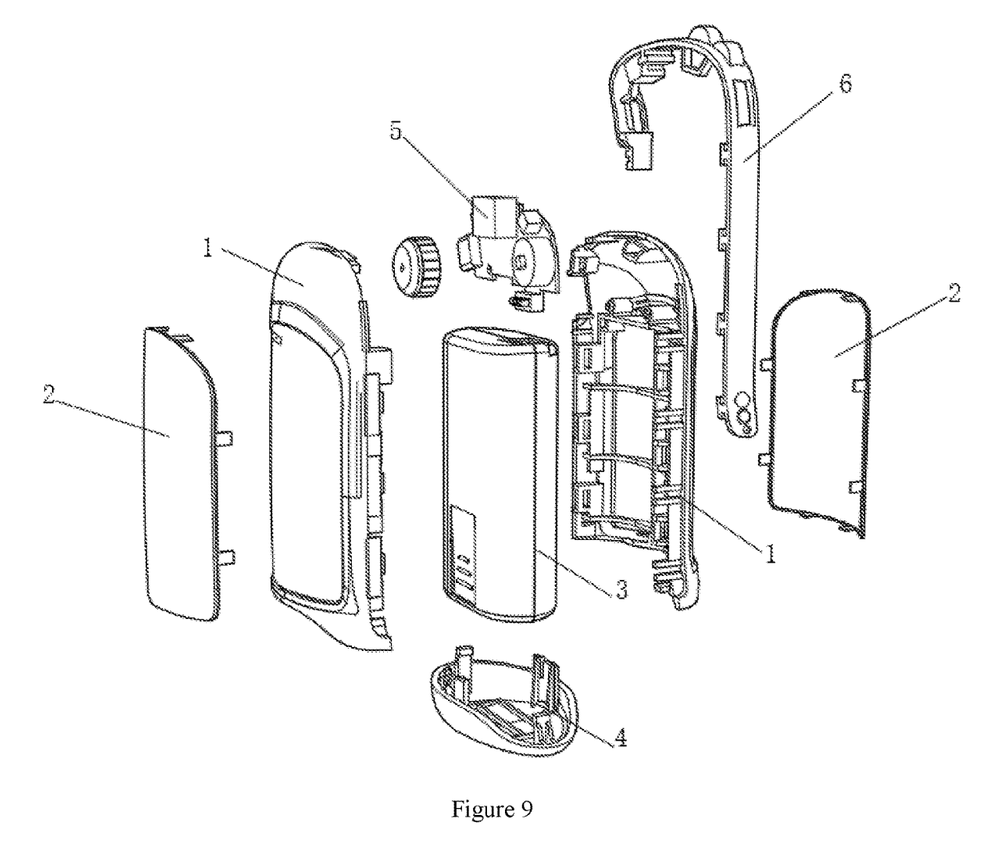
FIG. 9 is the third explosion diagram of the shell of the utility model.

Please refer to FIG. 1, FIG. 5 and FIG. 9. This embodiment provides a hand warmer with detachable battery, which includes a shell 1. The shell 1 is an injection molded part, and the outer side of the shell 1 is provided with a metal piece 2. The metal piece 2 is used as a heating part, and the mica plate (mica plate) is used for its good insulation performance and high temperature resistance. It takes the mica plate (plate) as a skeleton and insulation layer, and is supported and protected by galvanized or stainless steel plates. A PCB main board 5 is fixedly arranged in the housing 1, and the PCB main board 5 can be a PCBA circuit board or other circuit boards, as long as the hardware piece 2 can be controlled to heat.

A detachable battery compartment 3 is arranged inside the shell 1, and a storage battery is arranged inside the battery compartment 3, which can supply power to the PCB main board 5 and the hardware chip 2, so that the hardware chip 2 generates heat.

The shell 1 is also provided with a knob which can be rotated to control the working state of the hardware chip 2. The knob can be an encoder knob or a knob which can control the resistance, and can change the current, thus changing the working state of the hardware chip 2.

The bottom of the casing 1 is provided with an opening structure, and the battery is put into the casing 1 from the opening. The opening is clamped with a battery cover 4, and the battery cover 4 can be detached from the opening, so that the battery can be directly taken down and replaced.

The outer side of the shell 1 is also provided with silica gel 6, and silica gel 6 protects the shell, and the tightness of the shell joint can be ensured.

In this embodiment, the shell 1 is formed by splicing two plastic shells, and the silica gel 6 is arranged outside the joint seam of the shell 1. Because the joint of the shell 1 is in a bulged state, the silica gel 6 is arranged at the bulged position, which can protect the bulged position and prevent dust from entering the inside of the shell 1.

Figure 4:
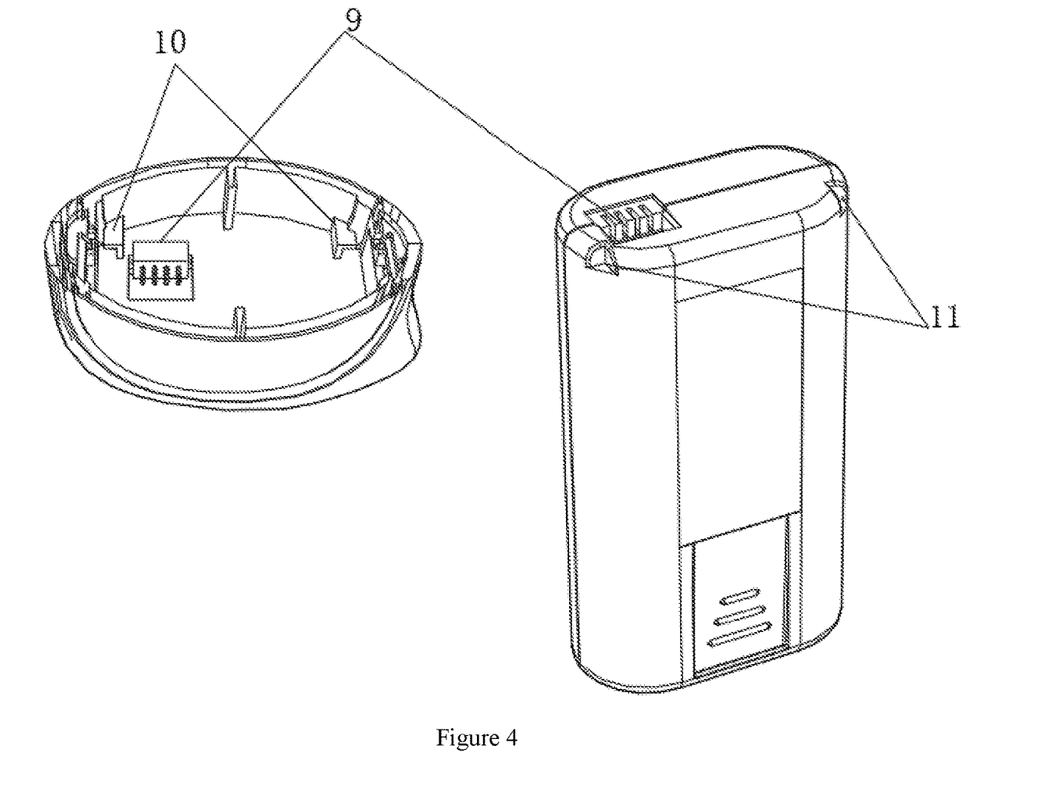
FIG. 4 is the positioning structure diagram of the battery compartment and shell of the utility model.
Figure 8:
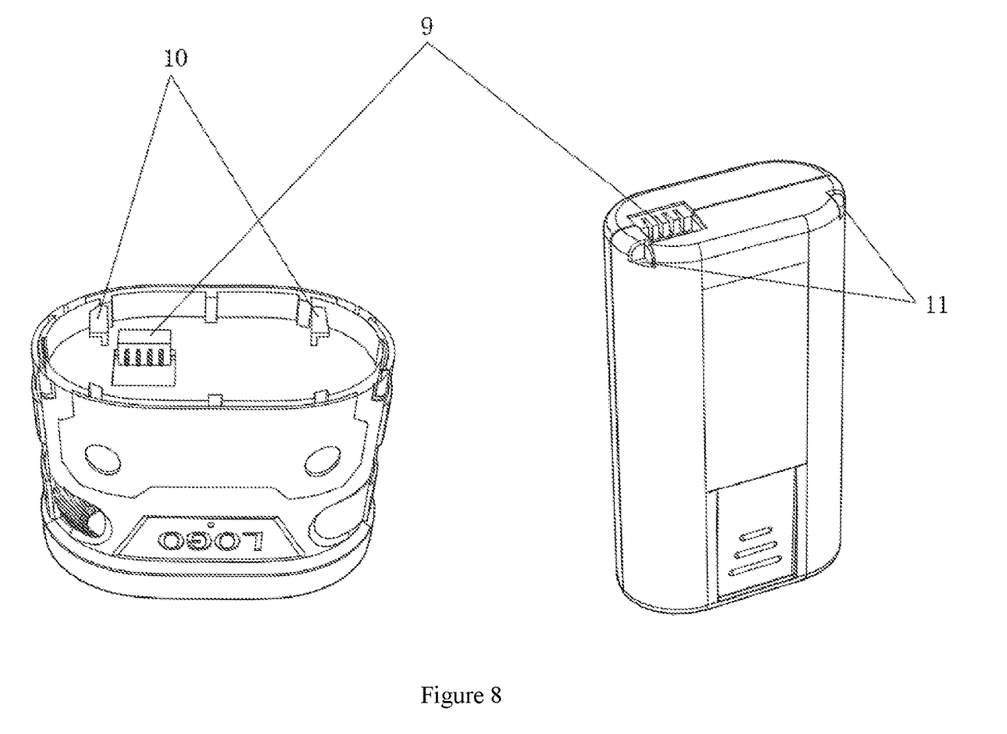
FIG. 8 is the positioning structure diagram of the battery compartment and shell of the utility model.

In this embodiment, as shown in FIGS. 4 and 8, a positioning point 10 is fixedly installed at the upper end of the inner side of the housing 1, and positioning grooves 11 matched with the positioning point 10 are formed at both sides of the top of the battery compartment 3. After the battery compartment 3 is installed in the housing 1, the positioning point 10 and the positioning groove 11 are clamped together to position the battery compartment 3.

The inside of the shell 1 and the battery compartment 3 are also provided with mutually matched charging interfaces 9. After the battery is installed, the charging interfaces will be connected to charge, and the battery can be used to supply power to the PCB main board and the hardware chip 2.

Figure 6:
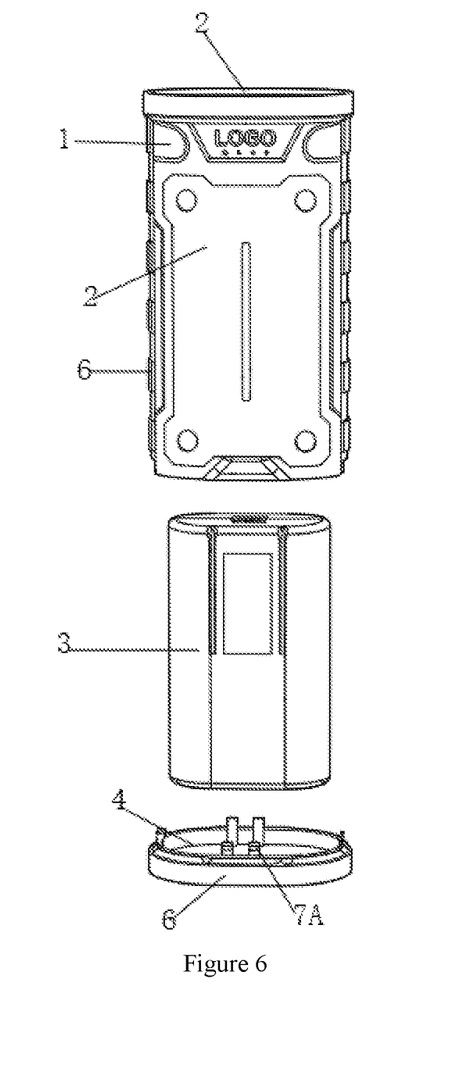
FIG. 6 is the disassembly diagram of another shell and battery compartment of the utility model.

In a further embodiment, as shown in FIGS. 5-6, the upper end of the housing 1 is further provided with an upper cover 12, and silica gel 6 is fixedly installed on the outer sides of the upper cover 12 and the battery cover 4. The silica gel 6 also has a protective effect on the upper cover 12 and the battery cover 4, especially when it is accidentally dropped on the ground during use. The silica gel has a buffering effect and can reduce the impact force.

The existing hand warmers also have replaceable batteries, and the battery covers are directly stuck on the hand warmers, so the installation is not firm. However, due to the large proportion of lithium battery, its mass and weight are relatively large. Therefore, when in use, under the gravity of the hand warmer battery, it is easy to open the battery cover, resulting in the battery falling out. Especially when hand warmers accidentally drop, the battery cover is easier to open under the impact force.

Figure 2:
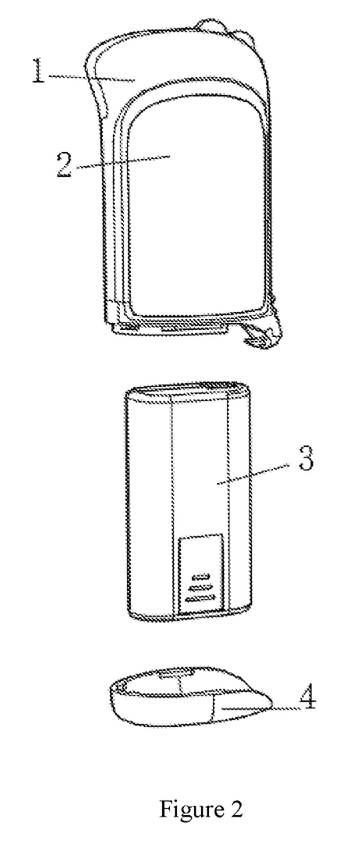
FIG. 2 is the disassembly diagram of the shell and battery compartment of the utility model.
Figure 3:
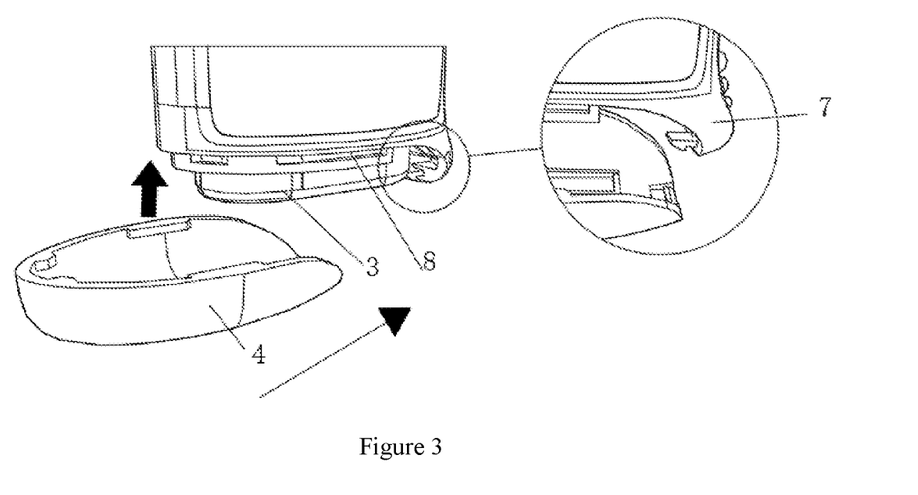
FIG. 3 is the installation schematic diagram of the battery cover and shell of the utility model.

One side of the bottom of the shell 1 is fixedly provided with a tail buckle 7 which protrudes outwards and has an arc structure, and the outer side of the shell 1 is also provided with a rail groove 8. As shown in FIGS. 1-3, the inner edge of the battery cover 4 is provided with a bump matched with the rail groove 8, and one side of the battery cover 4 is provided with a clamping groove matched with the tail buckle 7.

When installing, first align the battery cover 4 with the guide rail groove 8, then push the battery cover 4 inward, and align and clamp with the tail buckle 7 to install the plate battery cover 4. The tail part 7 also has the function of limiting the battery cover 4, preventing the battery cover 4 from falling off directly to the lower part, so that the battery cover 4 can be installed more firmly, and will not fall off even if it falls and is hit.

When opening the battery cover 4, it is necessary to slide the battery cover 4 horizontally outward, so that the battery cover 4 is separated from the guide groove 8, and the battery cover 4 will be separated from the tail buckle 7, so that the battery cover 4 can be removed.

Figure 7:
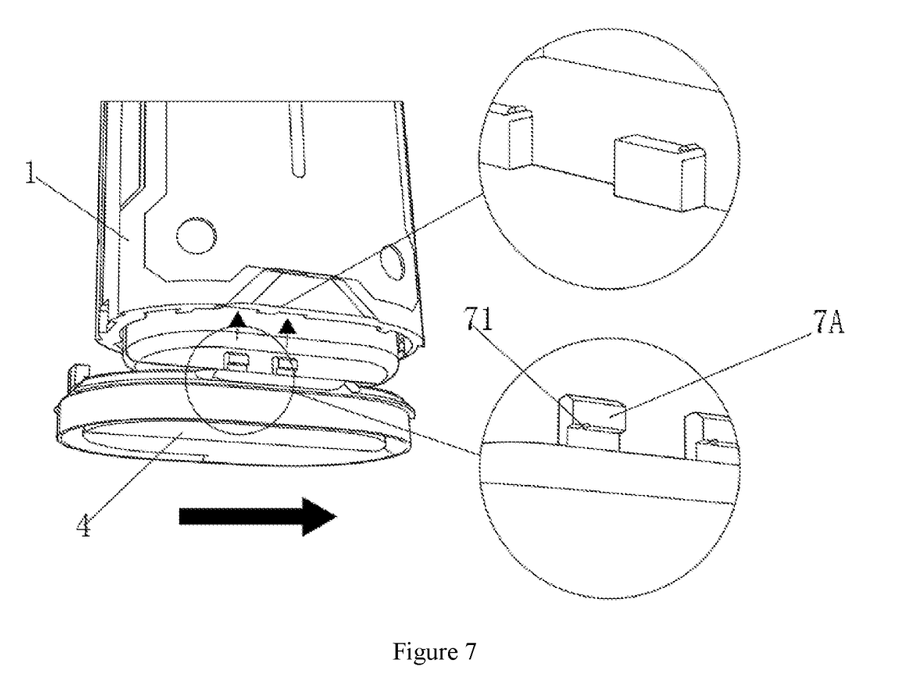
FIG. 7 is another installation schematic diagram of the battery cover and shell of the utility model.

In a further embodiment, the battery cover 4 can be installed in a sliding way. As shown in FIG. 6-7, the inner wall of the bottom of the housing 1 is provided with a clamping groove, and the top of the battery cover 4 is fixedly provided with a clamping block 7A matched with the clamping groove. The clamping block 7A can be directly inserted into the clamping groove, and positioning beads 71 are provided in both the clamping block 7A and the clamping groove. The width of the card slot is larger than that of the card block 7A. During installation, the clamping block 7A is inserted into the clamping slot, and then the battery cover 4 is pushed laterally, and the positioning beads are clamped together, so that the battery cover 4 can be installed. When removing the battery cover 4, push the battery cover 4 in the opposite direction to remove the battery cover 4.

The battery cover 4 is installed in two directions, which makes the installation more firm. When being impacted, the generated force is unidirectional, and the impact force will not open the battery cover 4.

Figure 10:
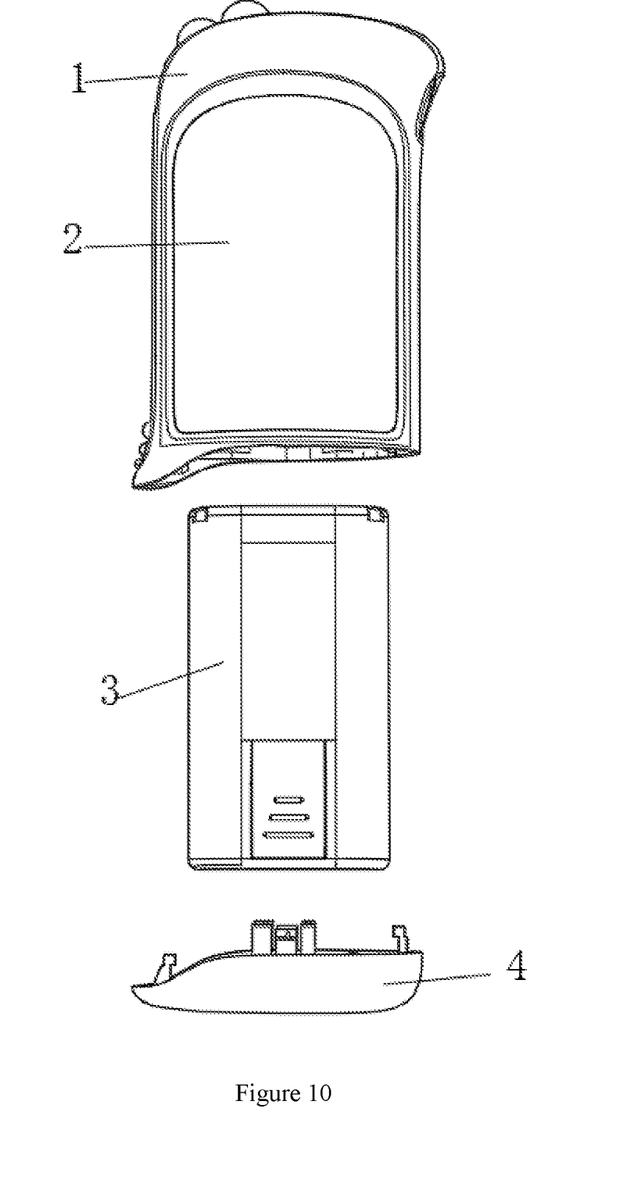
FIG. 10 is the disassembly diagram of the third shell and battery compartment of the utility model.
Figure 11:
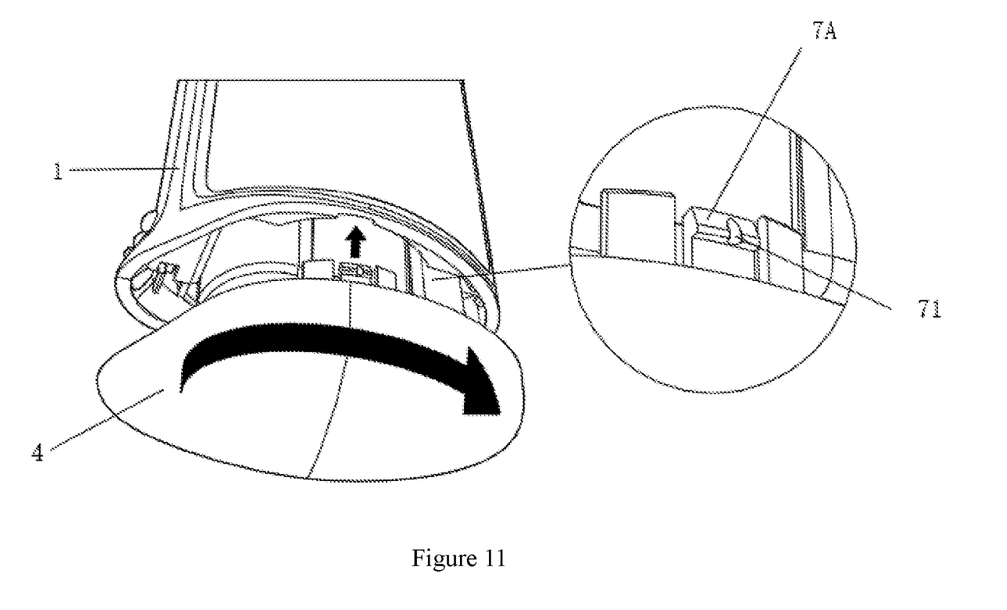
FIG. 11 is the third installation schematic diagram of the battery cover and shell of the utility model.

As shown in FIG. 9-11, the bottom inner side wall of the casing 1 is provided with a clamping groove, and the top of the battery cover 4 is fixedly provided with a clamping block 7A matched with the clamping groove, and positioning beads 71 are provided on the clamping block 7A and the clamping groove. During installation, the clamping block 7A is inserted into the clamping slot, and at the same time, the battery cover 4 is rotated clockwise, so that the positioning beads are clamped together and can be clamped in position.

When the hand warmer is used, the rotating connection card is applied with one-way force, and there is no rotating force. Therefore, the installation of the rotating connection card is stable.

Although the embodiments of the utility model have been shown and described, it can be understood by those skilled in the art that many changes, modifications, substitutions and variations can be made to these embodiments without departing from the principle and spirit of the utility model. The scope of the utility model is defined by the appended claims and their equivalents.

I claim:

1. A hand warmer with detachable battery comprising a shell (1), wherein an outer side of the shell (1) is provided with a hardware piece (2), an inner part of the shell (1) is fixedly provided with a PCB main board (5), and a detachable battery compartment (3) is also arranged in the shell (1);

wherein a bottom of the shell (1) is provided with an opening, the opening is clamped with a battery cover (4), and the battery cover (4) is detachable from the opening;

wherein the outer side of the shell (1) is also provided with silica gel (6); and     wherein an upper end of the inner side of the shell (1) is fixedly provided with a positioning point (10), two sides of a top of the battery compartment (3) are provided with positioning slots (11) matched with the positioning points (10), and the inside of the shell (1) and the battery compartment (3) are also provided with mutually matched charging interfaces (9) for supplying power to the PCB motherboard and hardware pieces (2).

2. The hand warmer with detachable battery according to claim 1, wherein the shell (1) is formed by splicing two plastic shells, and the silica gel (6) is arranged outside the joint of the shell (1).

3. The hand warmer with detachable battery according to claim 2, wherein an upper end of the shell (1) is also provided with an upper cover (12), and silica gel (6) is fixedly installed on the outer sides of the upper cover (12) and the battery cover (4).

4. The hand warmer with detachable battery according to claim 1, wherein one side of the bottom of the shell (1) is fixedly provided with a tail buckle (7) which protrudes outwards and has an arc structure, and the outer side of the shell (1) is also provided with a guide groove (8); and     wherein an inner edge of the battery cover (4) is provided with a bump matched with the rail groove (8), and one side of the battery cover (4) is provided with a clamping groove matched with the tail buckle (7).

5. The hand warmer with detachable battery according to claim 1, wherein an inner side wall of the bottom of the shell (1) is provided with a clamping slot, and a top of the battery cover (4) is fixedly provided with a clamping block (7A) matched with the clamping slot, and positioning beads (71) are provided on the clamping block (7A); and     wherein during installation, the clamping block (7A) is inserted into the clamping slot to laterally push the battery cover (4), and the positioning beads are clamped together.

6. The hand warmer with detachable battery according to claim 1, wherein the inner side wall of the bottom of the shell (1) is provided with a clamping slot, and the top of the battery cover (4) is fixedly provided with a clamping block (7A) matched with the clamping slot, and positioning beads (71) are provided on the clamping block (7A); and     wherein during installation, the clamping block (7A) is inserted into the clamping slot, and the battery cover (4) is rotated to clamp the positioning beads together.

\* \* \* \* \*